United States Patent [19]

Dufresne

[11] Patent Number: 5,260,332

[45] Date of Patent: Nov. 9, 1993

[54] CHOLESTEROL LOWERING COMPOUNDS

[75] Inventor: Claude Dufresne, East Brunswick, N.J.

[73] Assignee: Merci & Co., Inc., Rahway, N.J.

[21] Appl. No.: 832,550

[22] Filed: Feb. 7, 1992

[51] Int. Cl.[5] .................. A61K 31/335; C07D 319/08
[52] U.S. Cl. ..................................... 514/452; 549/363
[58] Field of Search ......................... 549/363; 514/452

[56] References Cited

U.S. PATENT DOCUMENTS 5,026,554  6/1991  Bartizal et al. ..................... 549/363

FOREIGN PATENT DOCUMENTS

0494622A1  7/1992  European Pat. Off. .

OTHER PUBLICATIONS

Baxter et al, Squalestatin 1, A Potent Inhibitor of Squalene Synthase Which Lowers Serum Cholesterol in Vivo, J. Biol. Chem., vol. 267, pp. 11705-11708 (1992).

Primary Examiner—Nicky Chan
Attorney, Agent, or Firm—Catherine A. Dolan; Joseph F. DePrima; Melvin Winokur

[57] ABSTRACT

New Zaragozic acids have been isolated from a culture of MF5465. These compounds and their derivatives are active as squalene synthetase inhibitors and are useful in the treatment of hypercholesterolemia.

18 Claims, No Drawings

CHOLESTEROL LOWERING COMPOUNDS

BACKGROUND OF THE INVENTION

Hypercholesterolemia is known to be one of the prime risk factors for ischemic cardiovascular disease, such as arteriosclerosis. Bile acid sequestrants have been used to treat this condition; they seem to be moderately effective but they must be consumed in large quantities, i.e. several grams at a time, and they are not very palatable.

MEVACOROD® (lovastatin), now commercially available, is one of a group of very active antihypercholesterolemic agents that function by limiting cholesterol biosynthesis by inhibiting the enzyme, HMG-COA reductase.

Squalene synthetase is the enzyme involved in the first committed step of the de novo cholesterol biosynthetic pathway. This enzyme catalyzes the reductive dimerization of two molecules of farnesyl pyrophosphate to form squalene. The inhibition of this committed step to cholesterol should leave unhindered biosynthetic pathways to ubiquinone, dolichol and isopentenyl t-RNA.

Previous efforts at inhibiting squalene synthetase have employed pyrophosphate or pyrophosphate analog containing compounds such as those described in P. Ortiz de Montellano et al, J. Med Chem. 20, 243 (1977) and E.J. Corey and R. Volante, J. Am. Chem. Soc., 98, 1291 (1976). S. Biller (U.S. Pat. No. 4,871,721) describes isoprenoid (phosphinylmethyl)phosphonates as inhibitors of squalene synthetase.

Recently certain nonphosphorous containing inhibitors of squalene synthetase have been isolated as natural products. These natural product inhibitors are described in U.S. Pat. Nos. 5,053,425; 5,055,487 and 5,026,554.

U.S. Pat. No. 5,026,554 describes a squalene synthetase inhibitor of structure:

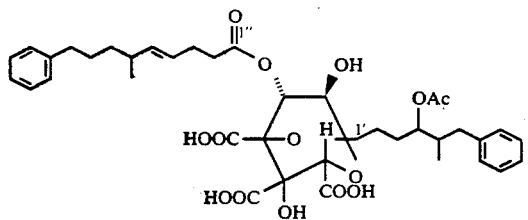

which is hereafter referred to as Zaragozic acid C. This compound is produced by a solid fermentation employing a culture of *Leptodontium elatius*. The present invention discloses certain structurally related compounds to Zaragozic acid C which have now been isolated from a fermentation broth using *Leptodontium elatius*.

DETAILED DESCRIPTION OF THE INVENTION

The present invention is directed to compounds of structural formula (I)

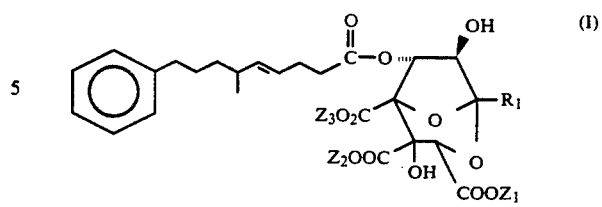

wherein
$R_1$ is selected from the group consisting of

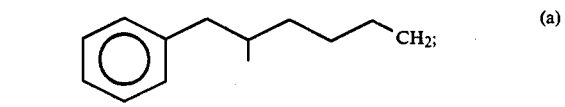

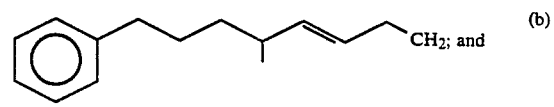

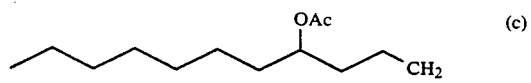

$Z_1$, $Z_2$ and $Z_3$ are each independently selected from;
a) H;
b) $C_{1-5}$alkyl;
c) $C1$-5alkyl substituted with a member of the group consisting of:
  i) phenyl,
  ii) phenyl substituted with methyl, methoxy, halogen (Cl, Br, I, F) or hydroxy; or
a pharmaceutically acceptable salt of a compound of of formula (I).

In one class of this invention are those compounds of formula (I) wherein
$R_1$ is

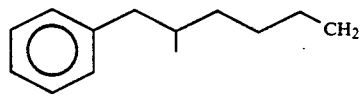

Further exemplifying this class is the compound wherein $Z_1$, $Z_2$ and $Z_3$ are each hydrogen or a pharmaceutically acceptable salt thereof. The compound wherein $Z_1$, $Z_2$ and $Z_3$ are each hydrogen is hereafter referred to as desacetoxy Zaragozic acid C.

In a second class of this invention are those compounds of formula (I) wherein $R_1$ is

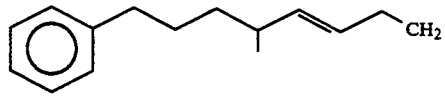

Further exemplifying this class is the compound wherein $Z_1$, $Z_2$ and $Z_3$ are each hydrogen or a pharmaceutically acceptable salt thereof. The compound wherein $Z_1$, $Z_2$ and $Z_3$ are each hydrogen is hereafter referred to as Zaragozic acid E.

In a third class of this invention are those compounds of formula (I) wherein
$R_1$ is

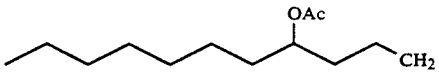

Further exemplifying this class is the compound wherein $Z_1$, $Z_2$ and $Z_3$ are each hydrogen or a pharmaceutically acceptable salt thereof. The compound wherein $Z_1$, $Z_2$ and $Z_3$ are each hydrogen is hereafter referred to as Zaragozic acid F.

The compounds of formula (I) are prepared in an aerobic fermentation procedure employing a fungal culture, MF5465, identified as *Leptodontium elatius*. The fermentation procedure employed is described in U.S. Pat. No. 5,026,554, the contents of which are herein specifically incorporated by reference.

The compounds of the present invention have been isolated as components produced in lower yield than Zaragozic acid C from this fermentation Mutants of MF5465, having essentially the same characteristics as MF 5465, are also capable of producing compounds of this invention.

The culture MF5465 is that of a fungus, a lignicolous Hyphomycete, *Leptodontium elatius*, isolated from wood in the Joyce Kilmer Memorial Forest in North Carolina. This culture has been deposited with the American Type Culture Collection at 12301 Parklawn Drive, Rockville, Md. 20852 as ATCC 74011.

The characteristics of MF5465 are described in U.S. Pat. No. 5,026,554.

Compounds of this invention can be obtained by culturing the above noted microorganism in an aqueous nutrient medium containing sources of assimilable carbon and nitrogen, preferably under aerobic conditions. Nutrient media may also contain mineral salts and defoaming agents.

The preferred sources of carbon in the nutrient medium are carbohydrates such as glucose, glycerin, starch, dextrin, and the like. Other sources which may be included are maltose, mannose, sucrose, and the like. In addition, complex nutrient sources such as oat flour, corn meal, millet, corn and the like may supply utilizable carbon. The exact quantity of the carbon source which is used in the medium will depend, in part, upon the other ingredients in the medium, but is usually found in an amount ranging between 0.5 and 5 percent by weight. These carbon sources can be used individually in a given medium or several sources in combination in the same medium.

The preferred sources of nitrogen are amino acids such as glycine, methionine, proline, threonine and the like, as well as complex sources such as yeast extracts (hydrolysates, autolysates), dried yeast, tomato paste, soybean meal, peptone, corn steep liquor, distillers solubles, malt extracts and the like. Inorganic nitrogen sources such as ammonium salts (eg. ammonium nitrate, ammonium sulfate, ammonium phosphate, etc.) can also be used. The various sources of nitrogen can be used alone or in combination in amounts ranging between 0.2 to 70 percent by weight of the medium.

The carbon and nitrogen sources are generally employed in combination, but need not be in pure form. Less pure materials which contain traces of growth factors, vitamins, and mineral nutrients may also be used. Mineral salts may also be added to the medium such as (but not limited to) calcium carbonate, sodium or potassium phosphate, sodium or potassium chloride, magnesium salts, copper salts, cobalt salts and the like.

Also included are trace metals such as manganese, iron, molybdenum, zinc, and the like. In addition, if necessary, a defoaming agent such as polyethylene glycol or silicone may be added, especially if the culture medium foams seriously.

The preferred process for production of compounds of this invention consists of inoculating spores or mycelia of the producing organism into a suitable medium and then cultivating under aerobic condition.

The fermentation procedure generally is to first inoculate a preserved source of culture into a nutrient seed medium and to obtain, sometimes through a two step process, growth of the organisms which serve as seeds in the production of the active compounds. After inoculation, the flasks are incubated with agitation at temperatures ranging from 20° to 30° C., preferably 25° to 28° C. Agitation rates may range up to 400 rpm, preferably 200 to 220 rpm. Seed flasks are incubated over a period of 2 to 10 days, preferably 2 to 4 days. When growth is plentiful, usually 2 to 4 days, the culture may be used to inoculate production medium flasks. A second stage seed growth may be employed, particularly when going into larger vessels. When this is done, a portion of the culture growth is used to inoculate a second seed flask incubated under similar conditions but employing shorter time.

After inoculation, the fermentation production medium is incubated for 3 to 30 days, preferably 7 to 21 days, with or without agitation (depending on whether liquid or solid fermentation media are employed). The fermentation is conducted aerobically at temperatures ranging from 20° to 40° C. If used, agitation may be at a rate of 200 to 400 rpm. To obtain optimum results, the temperatures are in the range of 22° to 28° C., most preferably 24° to 26° C. The pH of the nutrient medium suitable for producing the active compounds is in the range of 3.5 to 8.5, most preferably 5.0 to 7.5. After the appropriate period for production of the desired compound, fermentation flasks are harvested and the active compound isolated.

A water miscible organic solvent is employed to extract a compound of this invention from the solid fermentation medium. The preferred solvent for extraction of the solid fermentation is acetone. The mixture of organic solvent and fermentation broth is vigorously stirred and filtered, and water added to the filtrate. The aqueous extract is then adsorbed on an anion exchange resin. The preferred resin is AG4-X4 (formate). The active compound can be eluted from AG4-X4 using a low pH solution or a high salt eluant; the preferred eluant is 0.2N sulfuric acid in 60% acetonitrile water. After elution from the ion exchange resion, the active compound may be recovered from the eluate by diluting the eluate with water, and extracting into an organic solvent; the preferred solvent for extraction is ethyl acetate. The organic extract is then evaporated to afford partially purified active compound.

The active compound is further purified by chromatographic separation which may be carried out by employing reverse phase chromatography. The preferred adsorbent for this chromatography is a C8 bonded phase silica gel. The preferred eluant for reverse phase chromatography is a mixture of acetonitrile and water buffered at a low pH, such as 0.1% phosphoric acid, or trifluoroacetic acid.

The present invention is also directed to a method of treating hypercholesterolemia which comprises the administration to a subject in need of such treatment a nontoxic therapeutically effective amount of a compound represented by structural formula (I) and pharmaceutically acceptable salts thereof. Specifically, the compounds of this invention are useful as antihypercholesterolemic agents for the treatment of arteriosclerosis, hyperlipidemia, familial hypercholesterolemia and the like diseases in humans. They may be administered orally or parenterally in the form of a capsule, a tablet, an injectable preparation or the like. It is usually desirable to use the oral route. Doses may be varied, depending on the age, severity, body weight and other conditions of human patients, but daily dosage for adults is within a range of from about 20 mg to 2000 mg (preferably 20 to 100 mg) which may be given in two to four divided doses. Higher doses may be favorably employed as required.

The present invention is also directed to a method of inhibiting squalene synthetase which comprises the administration to a subject in need of such treatment a nontoxic therapeutically effective amount of a compound represented by structural formula (I) and pharmaceutically acceptable salts thereof. Specifically, the compounds of this invention are useful in treating disease conditions such as, but not limited to, hypercholesterolemia which result from the action of the enzyme squalene synthetase. They may be administered orally or parenterally in the form of a capsule, a tablet, an injectable preparation or the like. It is usually desirable to use the oral route. Doses may be varied, depending on the age, severity, body weight and other conditions of human patients, but daily dosage for adults is within a range of from about 20 mg to 2000 mg (preferably 20 to 100 mg) which may be given in two to four divided doses. Higher doses may be favorably employed as required.

The pharmaceutically acceptable salts of the compounds of this invention include those formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylenediamine, chloroprocaine, diethanolamine, procaine, N-benzylphenethylamine, diethylamine, piperazine, tris(l,iydrowjmethyl)aminomethane, and tetramethylammonium hydroxide. The salts included herein encompass those wherein one, two or all three of the carboxyl groups are in the salt form.

The compounds of this invention may also be administered in combination with other cholesterol lowering agents such as those which inhibit an enzymatic pathway in the biosynthesis of cholesterol. Example of such agents would include but are not limited to HMG-COA reductase inhibitors, HMG-COA synthase inhibitors, and squalene epoxidase inhibitors. Illustrative of such inhibitors are lovastatin, simvastatin, pravastatin and fluvastatin. Other cholesterol lowering agents that may be administered include niacin, probucol, and the fibric acids, clofibrate and gemfibrozil. Appropriate daily dosages for adults are niacin (2-8 gm), probucol (up to 1000 mg), clofibrate (up to 2 gm) and gemfibrozil (800-1500 mg).

The compounds of this invention may also be coadministered with pharmaceutically acceptable nontoxic cationic polymers capable of binding bile acids in a non-reabsorbable form in the gastrointestinal tract. Examples of such polymers include cholestyramine, colestipol and poly[methyl-(3-trimethylaminopropyl)imino-trimethylene dihalide]. The relative amounts of the compounds of this invention and these polymers is between 1:100 and 1:15,000.

The intrinsic squalene synthetase inhibitory activity of representative compounds of this invention was measured by the standard in vitro protocol described below:

Preparation of Microsomes

Male, Charles River CD rats (120 to 150 g) were fed a diet containing 0.1% lovastatin for 4 days. The livers from these rats were homogenized in 5 volumes (ml/g) of ice cold 50 mM HEPES (4-(2-hydroxyethyl)-1-piperazine-ethanesulfonic acid), 5 mM EDTA(ethylenediaminetetraacetic acid) pH 7.5 with a Potter-Elvehjem type tissue grinder. The homogenate was centrifuged twice at 20,000×g for 15 minutes at 4° C., discarding the pellet each time. The supernatant was then centrifuged at 100,000×g for 1 hour at 4° C. The resulting microsomal pellet was resuspended in a volume of the above homogenizing buffer equal to one-fifth the volume of the original homogenate. This microsomal preparation has a protein concentration of about 7 mg/ml. The microsomal suspensions were stored in aliquots at −70° C. Squalene synthetase activity in these aliquots is stable for at least several months.

Partial Purification of Prenyl Transferase

Prenyl transferase was purified to use in the enzymatic synthesis of radiolabelled farnesyl pyrophosphate. Prenyl transferase was assayed by the method of Rilling (Methods in Enzymology 110, 125-129 (1985)) and a unit of activity is defined as the amount of enzyme that will produce 1 μmole of farnesyil pyrophosphate per minute at 30° in the standard assay.

The livers of 23 forty-day old male rats that had been fed 5% cholestyramine plus 0.1% lovastatin were homogenized in a Waring blender in 1 liter of 10 mM mercaptoethanol, 2 mM EDTA, 25 μm leupeptin, 0.005% phenylmethyl sulfonyl fluoride pH 7.0 containing 0.1 trypsin inhibitor units of aprotinin/ml. The homogenate was centrifuged at 20,000 ×g for 20 minutes. The supernatant was adjusted to pH 5.5. with 6N HOAC and centrifuged at 100,000 ×g for 1 hour. This supernatant was adjusted to pH 7.0 with 3N KOH and a 35-60% ammonium sulfate fraction taken. The 60% pellet was redissolved in 60 ml of 10 mM potassium phosphate, 10 mM mercaptoethanol, 1 mM EDTA pH 7.0 (Buffer A) and dialyzed against two 1 liter changes of Buffer A. This dialyzed fraction was applied to a 12.5 ×5 cm column of DEAE-sepharose 4B equilibrated with Buffer A. The column was washed with 700 ml of Buffer A and a 1 liter gradient from Buffer A to 100 mM potassium phosphate, 10 mM mercaptoethanol, 1 mM EDTA pH 7.0. Fractions having a specific activity greater than 0.20 units/mg were combined, solid ammonium sulfate was added to bring to 60% saturation and pelleted. The pellet was dissolved in 8 ml of 10 mM Tris, 10 mM β-mercaptoethanol pH 7.0 (Buffer B). The redissolved pellet was taken to 60% saturation with ammonium sulfate by adding 1.5 volumes of saturated ammonium sulfate in Buffer B. This ammonium sulfate suspension contained 3.5 units/ml with a specific activity of 0.23 units/mg and was free of isopentenyl pyrophosphate isomerase activity. This ammonium sulfate suspension was used for the synthesis of [4-$^{14}$C.]farnesyl-pyrophosphate and its activity was stable stored at 4° C. for at least 6 months.

Enzymatic Synthesis of [4-$^{14}$C] farnesyl-Pyrophosphate

The solvent (ethanol. 0.15 N NH$_4$OH, 1:1) was removed from 55 μCi of [4-$^{14}$C.]isopentenyl pyrophosphate(47.9 μCi/μmole) by rotary evaporation. Six hundred microliters of 100 MM Tris, 10 mM MgCl$_2$, 4 mM dithiothreitol pH 7.5 was added and the solution was transferred to a 1.5 ml Eppendorf centrifuge tube. Geranyl-pyrophosphate, 250 μl of a 20 mM solution, and 50 μl of the ammonium sulfate suspension of prenyl transferase were added to initiate the reaction. This incubation contained 5 [μmoles of geranyl pyrophosphate, 1.15 μmoles of isopentenyl pyrophosphate, 6 μmoles of MgCl$_2$ of 0.18 units of prenyl transferase in a volume of 900 μl. The incubation was conducted at 37° C. During the incubation, the mix turned cloudy white as the newly formed magnesium complex of farnesyl pyrophoshate precipitated out of solution. The (4-$^{14}$C.] farnesyl pyrophosphate was collected by centrifugation for 3 minutes at 14,000 rpm in an Eppendorf centrifuge tube, the supernatant removed, and the pellet was dissolved in 1.0 ml of 50 mM HEPES, 5 mM EDTA, pH 7.5 The yield was 50.7 μCi (92%) of [4-$^{14}$C.]farnesyl pyrophosphate. The [4-$^{14}$C.]farnesyl pyrophosphate was stored in aliquots at −70° C.

SQUALENE SYNTHETASE ASSAY

Reactions were performed in 16 ×125 mm screw cap test tubes. A batch assay mix was prepared from the following solution:

| | | ml per assay | volume for 50 assays |
|---|---|---|---|
| 1. | 250 mM Hepes pH 7.5 | 20 | 1000 |
| 2. | NaF 110 mM | 10 | 500 |
| 3. | MgCl$_2$ 55 mM | 10 | 500 |
| 4. | Dithiothreitol 30 mM | 10 | 500 |
| 5. | NADPH 10 mM (made fresh) | 10 | 500 |
| 6. | [4-$^{14}$C]farnesyl-pyrophosphate 47.9 μCi/μmole. and 0.025 μCi/3.0 μl | 3.0 | 150 |
| 7. | H$_2$O | 24 | 1200 |

This assay mix was degassed under a vacuum and flushed with N$_2$. Solutions of the squalene synthetase inhibitors were prepared either in DMSO or MeOH and a 1:120 dilution of the microsomal protein was made with the original homogenizing buffer. For each reaction, 87 μl of the assay mix was taken with 3 μl of an inhibitor solution (DMSO or MeOH in the controls), warmed to 30,C. in a water bath and then the reaction was initiated by the addition of 10 μl of the 1:120 dilution of microsomal protein (0.6 μg protein total in the assay). The reactions were stopped after 20 minutes by the addition of 100 μl of a 1:1 mix of 40% KOH with 95% EtOH. The stopped mix was heated at 65° C. for 30° minutes, cooled, 10 ml of heptane was added and the mix was vortexed. Two g of activated alumina was then added, the mix vortexed again, the alumina allowed to settle and 5 ml of the heptane layer was removed. Ten ml of scintillation fluid was added to the heptane solution and radioactivity was determined by liquid scintillation counting.

Percent inhibition is calculated by the formula:

$$1 - \frac{[Sample - Blank]}{[Control - Blank]} \times 100$$

IC$_{50}$ values were determined by plotting the log of the concentration of the test compound versus the percentage inhibition. The IC$_{50}$ is the concentration of inhibitor that gives 50% inhibition as determined from these plots.

Representative compounds of this invention exhibited IC$_{50}$ values which were all <5nM.

The present compounds also demonstrate broad spectrum antifungal activity as determined by broth and agar dilution methods. Thus the present invention is also directed to a method of treating fungus infections which comprises the administration to an organism in need of such treatment a nontoxic therapeutically effective amount of a compound represented by the structural formula (I) and pharmaceutically acceptable salts thereof. Generally from 2 to about 20 mg/kg should be employed as a unit dosage in an antifungal treatment.

Furthermore the compounds of the present invention have been found to be inhibitors of farnesyl-protein transferase and thereby of farnesylation of the RAS protein and thus block the ability of RAS to transform normal cells to cancer cells. Farnesyl-protein transferase activity may be reduced or completely inhibited by adjusting the compound dose.

The intrinsic farnesyl-protein transferase (FTase) activity of representative compounds of this invention is measured by the assays described below:

RASIT ASSAY I

Farnesyl-protein transferase (Ftase) from bovine brain is chromatographed on DEAE-Sephacel (Pharmacia, 0–0.8 M NaCl gradient elution), N-octyl agarose (Sigma, 0–0.6 M Nacl gradient elution), and a mono Q HPLC column (Pharmacia, 0–0.3 M NaCl gradient). Ras-CVLS at 3.5 μM, 0.25 μM [$^3$H]FPP, and the indicated compounds are incubated with this partially purified enzyme preparation.

RASIT ASSAY II

Farnesyl-protein transferase (Ftase) from bovine brain was chromatographed on DEAE-Sephacel (Pharmacia, 0–0.8 M NaCl gradient elution), N-octyl agarose (Sigma, 0–0.6 M Nacl gradient elution), and a mono Q HPLC column (Pharmacia, 0–0.3 M NaCl gradient). Ras-CVLS at 1.0 μM, 0.5 μM [$^3$H]FPP, and the indicated compounds were incubated with this partially purified enzyme preparation. The Ftase data is a measurement of the ability of the test compound to inhibit Ras farnesylation in vitro.

The pharmaceutical compositions containing the compounds of structural formula I inhibit farnesyl-protein transferase and the farnesylation of the oncogene protein Ras. These compounds are useful as pharmaceutical agents for mammals, especially for humans. These compounds may be administered to patients for use in the treatment of cancer. Examples of the type of cancer which may be treated with the compounds of this invention include, but are not limited to, colorectal carcinoma, exocrine pancreatic carcinoma, and myeloid leukemias.

The present invention also encompasses a method of the treatment of cancer, comprising the administration of a pharmaceutical composition comprising a therapeutically effective amount of the compounds of this invention, with or without pharmaceutically acceptable carriers or diluents.

Suitable compositions of this invention include aqueous solutions comprising compounds of this invention and pharmacologically acceptable carriers, e.g. saline, at a pH level, e.g., 7.4. The solutions may be introduced into a patient's intramuscular blood-stream by local bolus injection.

When a compound according to this invention is administered into a human subject, the daily dosage will normally be determined by the prescribing physician with the dosage generally varying according to the age, weight, and response of the individual patient, as well as the severity of the patient's symptoms.

In one exemplary application, a suitable amount of compound is administered to a human patient undergoing treatment for cancer. Administration occurs in an amount between about 0.1 mg/kg of body weight to about 20 mg/kg of body weight of a mammal per day, preferably of between 0.5 mg/kg of body weight to about 10 mg/kg of body weight of a mammal a day.

The following examples illustrate the preparation of the compounds of formula (I) and their incorporation into pharmaceutical compositions and, as such, are not to be considered as limiting the invention set forth in the claims appended hereto.

EXAMPLE 1

Preparation of Desacetoxy Zaragozic acid C, Zaragozic acid E and Zaragozic acid F A. Culturinz MF 5465

Culture MF 5465, inoculated from frozen vegetative mycelia, was grown in KF seed medium flasks for 73 hours at 25C., 220 rpm, 85% humidity (U.S. Pat. No. 5,026,554). The KF flasks were pooled and the seed was used to inoculate 256 Fl production medium flasks (U.S. Pat. No. 5,026,554). Care was taken to manually distribute seed growth throughout the solid production medium. Production flasks were incubated statically at 25° C. for 22 days. Flasks were harvested as follows: 50 mls acetone were added to each production flask; growth was manually broken apart into small fragments by use of a glass pipette; flasks were re-stoppered and placed onto a gyrotory shaker and agitated for 30 minutes at 220 rpm while the extraction proceeded. After shaking, the contents of the individual flasks were pooled by pouring the solvent-extract off the mycelial covered corn into a 2 liter Erlermeyer flask. Several of these 2 liter flasks were then pooled together to yield 12.2 L of acetone extract.

B. Isolation

Fermentation batches as described above were extracted with acetone and then combined and filtered to give 11 L of extract. A portion of the extract (9.5 L) was concentrated under reduced pressure to 4.8 L. The concentrated aqueous acetone extract was then loaded onto an ion exchange column (125 ml resin bed; BioRad AG4-X4; formate cycle; pH 4.5) with a flow rate of 10-15 ml/min. The column was then washed with 1 L of 60 mM sodium formate in 60:40 acetonitrile/water (pH 4.5). (The sodium formate solution was prepared as follows. A 2 N formic acid solution in water was adjusted to pH 3 with NAOH. A 30 ml aliquot was then added to 370 ml of water, followed by dilution with 600 ml acetonitrile. The resulting solution then has an apparent pH of 4.5.) The column was subsequently eluted with 200 mm sulfuric acid in 60:40 acetonitrile/water, collecting 250 ml fractions. Fractions 3-6 were combined and extracted with 1 L ethyl acetate. The ethyl acetate layer was separated, dried over anhydrous sodium sulfate, and evaporated to dryness to yield a dark residue (784 mg). The residue was then dissolved in 2:2:0.4 methanol/acetonitrile/water to give 4.7 ml of solution A. A 2 ml portion of solution A was injected on a prep HPLC (Dynamax C8 column; 60 A, 8 um; 21.4 mm ID ×250 mm with guard column) eluting at 10 ml/min (75% acetonitrile/25% 0.1% phosphoric acid in water; pH 2.5) and fractions were collected at 0.5 min intervals. Fractions 41-57 were combined. The remaining 2.7 ml portion of solution A was injected on the same HPLC column, as previously described, and fractions 36-58 were combined. The combined fractions from both runs were combined and extracted with an equal volume of ethyl acetate. The ethyl acetate layer was separated, dried over anhydrous sodium sulfate, and evaporated to dryness. The residue was dissolved in 0.5 ml MeOH and injected onto a reverse phase HPLC column (Dynamax C8, 60 A, 8 um; 10 mM ID ×250 mM with guard column) eluting at 4 ml/min (70% acetonitrile/30% 0.1% phosphoric acid in water; pH 2.5). Fractions were collected at 1 min intervals. Fraction 15 was extracted with an equal volume of ethyl acetate and the ethyl acetate layer evaporated to dryness to afford desacetoxy Zaragozic acid C. Fraction 20 was extracted with an equal volume of ethyl acetate and the ethyl acetate layer evaporated to dryness to afford Zaragozic acid F. Fraction 22 was extracted with an equal volume of ethyl acetate and the ethyl acetate layer evaporated to dryness to afford Zaragozic acid E. The preparative HPLC fractionation can be monitored using analytical HPLC. Using a Dynamax 60 A, 8 um, C8 column (4.6 mm×250 mm; with guard; ca 26° C.) eluting at 1.0 ml/min with 70% acetonitrile/30% (0.1% phosphoric acid in water), the following retention times were observed:

| | |
|---|---|
| Desacetoxy zaragozic acid C: | 12.2 min |
| Zaragozic acid F: | 15.5 min |
| Zaragozic acid E: | 17.2 min |

Physical Characteristics

All NMR data was obtained at 25.0° C. using $CD_3OD$ as the solvent.

Desacetoxy Zaragozic Acid C $^1H$(500 MHz): 7.24(m,4H), 7.12(m,6H), 6.22(d,2.0), 5.36(dt,15.0,6.5), 5.30(dd,15.0,7.5), 5.24(s), 4.03(d,2.0), 2.62(dd,13.0,5.5), 2.56(m,2H), 2.34(m, 3H), 2.26(m, 2H), 2.06(sext, 7.0), 1.88(m,2H), 1.73(br oct, 6.0), 1.6-1.2(m,10H), 0.93(d,7.0, 3H), 0.83 (d, 6.5, 3H).

$^{13}C$ (125 MHz): 173.10, 172.53, 170.25, 168.57, 143.92, 142.75, 138.84, 130.21 (2), 129.41 (2), 129.26 (2), 129.10 (2), 127.61, 126.64 (2), 107.38, 90.98, 82.04, 81.25, 76.63, 75.66, 44.65, 37.83, 37.68, 37.62, 36.92, 36.62, 36.22, 35.38, 30.50, 28.78, 28.42, 24.04, 21.23, 19.82. Mass Spec; Negative ion FAB found 695 [M-HI(MW696, $C_{38}H_{48}O_{12}$),

ZARAGOZIC ACID E $^1H$(500 MHz): 7.24 (m, 4H), 7.12 (m, 6H), 6.22 (d, 2.0), 5.43 (dt, 15.0 6.5), 5.36 (dt, 15.0, 6.5), 5.31 (dd, 15.0, 7.5), 5.30 (dd, 15.0, 7.5), 5.24 (s), 4.03 (d, 2.0), 2.56 (m, 4H), 2.33 (m, 3H), 2.27 (m, 3H), 2.07 (sext, 7.0, 2H), 1.94 (m, 2H), 1.57 (m, 4H), 1.28 (m, 4H), 0.94 (d, 6.0, 3H), 0.93 (d, 6.5, 3H).

$^{13}C$ (125 MHz): 173.11, 172.48, 170.22, 168.54, 143.98, 143.93, 138.86, 137.69, 129.42 (2), 129.41 (2), 129.27 (2), 129.26, 129.25 (2), 127.62, 126.63, 126.61, 107.07, 91.03, 82.17, 81.23, 76.64, 75.66, 37.93, 37.82, 37.80, 37.63, 36.98, 36.92, 36.75, 35.37, 30.52, 30.50, 28.78, 26.97, 21.40, 21.24. Mass Spec: Negative ion FAB found 711 [M-E] (MW 712, $C_{40}H_{40}O_{12}$)

ZARAGOZIC ACID F $^1H$ (500 MHz): 7.23 (m, 2H), 7.12 (m, 3H), 6.22 (d, 2.0), 5.37 (dt, 15.1, 6.0), 5.31 (dd, 15.1, 7.5), 5.23 (s), 4.88 (m), 4.02 (d, 2.0), 2.56 (m, 2H), 2.34 (m, 2H), 2.26 (m, 2H), 2.07 (sext, 6.9), 2.02 (s, 3H), 1.88 (m, 2H), 1.58 (m, 8H), 1.3 (m, 12H), 0.93 (d, 7.0, 3H), 0.89 (t, 6.9, 3H).

$^{13}C$ (125 MHz): 173.18, 173.05, 172.5, 170.38, 168.73, 143.93, 138.83, 129.42 (2), 129.27 (2), 127.66, 126.64, 107.12, 91.0, 82.36, 81.30, 76.73, 75.69, 75.65, 37.84, 37.64, 36.93, 36.51, 35.40, 35.32, 35.19, 32.97, 30.57, 30.48, 30.34, 28.82, 26.48, 23.69, 21.25, 21.20, 19.75, 14.41. Mass Spec: Negative ion FAB found 733 [M-H] (MW 734, $C_{38}H_{54}O_{14}$).

EXAMPLE 2

Preparation of an Ammonium Salt

A 0.1 mmol sample of the free acid of a compound of formula (I) is dissolved in 10 ml of ethyl acetate. The resulting solution is saturated with gaseous ammonia upon which the ammonium salt precipitates from solution.

EXAMPLE 3

Preparation of a Potassium Salt

A solution of 0.1 mmol of the free acid of a compound of formula (I) in 10 ml of methanol is treated with an aqueous or methanolic solution containing 0.3 mmol of potassium hydroxide. Evaporation of the solvent affords the tri-potassium salt. Addition of between 0.1 and 0.3 mmol of potassium hydroxide yields analogously mixtures of the mono-potassium, di-potassium and tri-potassium salts whose composition depends upon the exact amount of potassium hydroxide added. In a similar fashion the sodium and lithium salts can be formed.

EXAMPLE 4

Preparation of a Calcium Salt

A solution of 0.1 mmol of the free acid of a compound of formula (I) in 20 ml of 6:4 methanol/water is treated with an aqueous solution of 0.1 mmol of calcium hydroxide. The solvents are evaporated to give the corresponding calcium salt.

EXAMPLE 5

Preparation of an Ethylenediamine Salt

A solution of 0.1 mmol of the free acid of a compound of formula (I) in 10 ml of methanol is treated with 0.1 mmol of ethylenediamine. Evaporation of the solvent affords the ethylenediamine salt. The procedure can also be applied to the preparation of the N,NII-dibenzylethylenediamine salt.

EXAMPLE 6

Preparation of a Tris(hydroxymethyl) aminomethane Salt

To a solution of 0.1 mmol of the free acid of a compound of formula (I) in 10 ml of methanol is added from 0.1 to 0.3 mmol of tris(hydroxymethyl) aminomethane dissolved in 10 ml of methanol. Evaporation of the solvent gives a corresponding salt form, the exact composition of which is determined by the molar ratio of amine added. Similarly prepared are the salts of L-ornithine, L-lysine, and N-methylgluacamine.

EXAMPLE 7

Preparation of an L-arzinine Salt

A solution of 0.1 mmol of the free acid of a compound of formula (I) in 20 ml of 6:4 methanol/water is treated with an aqueous solution of 0.1 to 0.3 mmol of L-arginine. Evaporation of the solvent affords the title salt, the exact composition of which is determined by the molar ratio of amino acid to the free acid of formula (I) used. Similarly prepared are the salts of L-ornithine, L-lysine and N-methylglucamine.

EXAMPLE 8

Preparation of A trimethyl ester

A solution of 2 mg of a free acid of compound of formula (I) in 0.5 ml of acetonitrile is treated at room temperature with 10 equivalents of DBU and 10 equivalents of MeI. After 2 hours the reaction is diluted with 10 ml of dichloromethane and washed successively with 10 ml of 0.1 M phosphoric acid, 10 ml of water, 10 ml of saturated sodium bicarbonate and 10 ml of water. After drying over sodium sulfate, the organic layer is concentrated and the residue is chromatographed on silica gel using mixtures of hexane and ethyl acetate to give a trimethyl ester.

The method of Example 8 is also suitable for the preparation of other ester derivatives such as 1) ethyl and other lower alkyl esters and 2) benzyl and substituted benzyl esters.

What is claimed is:

1. A compound of structural formula (I)

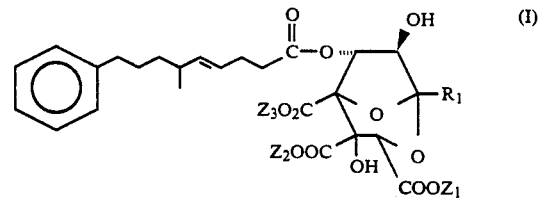

wherein
$R_1$ is selected from the group consisting of

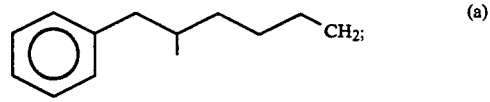

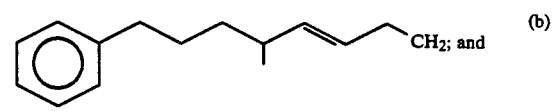

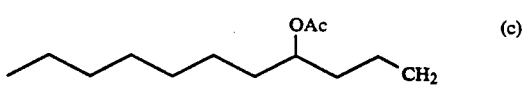

$Z_1$, $Z_2$ and $Z_3$ are each independently selected from;
  a) H;
  b) $C_{1-5}$alkyl; and
  c) $C_{1-5}$alkyl substituted with a member of the group consisting of:
    i) phenyl, and ii) phenyl substituted with methyl, methoxy, halogen (Cl, Br, I, F) or hydroxy; or
a pharmaceutically acceptable salt of a compound of formula (I).

2. A compound of claim 1 wherein $R_1$ is

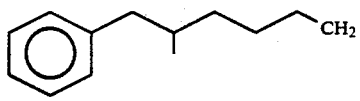

3. A compound of claim 2 wherein $Z_1$, $Z_2$ and $Z_3$ are each hydrogen, or a pharmaceutically acceptable salt thereof.

4. A compound of claim 1 wherein $R_1$ is

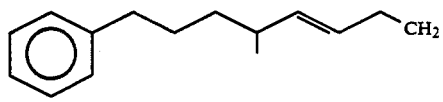

5. A compound of claim 4 wherein $Z_1$, $Z_2$ and $Z_3$ are each hydrogen, or a pharmaceutically acceptable salt thereof.

6. A compound of claim 1 wherein $R_1$ is

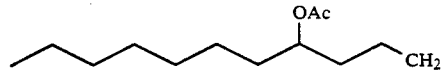

7. A compound of claim 6 wherein $Z_1$, $Z_2$ and $Z_3$ are each hydrogen, or a pharmaceutically acceptable salt thereof.

8. A compound of molecular formula $C_{38}H_{48}O_{12}$ and molecular weight 696 characterized by the
   (a) $^{13}C$ NMR chemical shifts, as measured in $CD_3OD$: 173.10, 172.53, 170.25, 168.57, 143.92, 142.75, 138.84, 130.21 (2), 129.41 (2), 129.26 (2), 129.10 (2), 127.61, 126.64 (2), 107.38, 90.98, 82.04, 81.25, 76.63, 75.66, 44.65, 37.83, 37.68, 37.62, 36.92, 36.62, 36.22, 35.38, 30.50, 28.78, 28.42, 24.04, 21.23, 19.83;
   (b) $^1H$ NMR chemical shifts, as measured in $CD_3OD$: 7.24(m,4H), 7.12(m,6H), 6.22(d,2.0), 5.36(dt,15.0,6.5), 5.30(dd,15.0,7.5), 5.24(s), 4.03(d,2.0), 2.62(dd,13.0,5.5), 2.56(m,2H), 2.34(m, 3H), 2.26(m, 2H), 2.06(sext, 7.0), 1.88(m,2H), 1.73(br oct, 6.0), 1.6 - 1.2(m,10H), 0.93(d,7.0, 3H), 0.83 (d, 6.5, 3H).

9. A compound of molecular formula $C_{40}H_{40}O_{12}$ and molecular weight 712 characterized by the
   (a) $^{13}C$ NMR chemical shifts, as measured in $CD_3OD$: 173.11, 172.48, 170.22, 168.54, 143.98, 143.93, 138.86, 137.69, 129.42 (2), 129.41 (2), 129.27 (2), 129.26, 129.25 (2), 127.62, 126.63, 126.61, 107.07, 91.03, 82.17, 81.23, 76.64, 75.66, 37.93, 37.82, 37.80, 37.63, 36.98, 36.92, 36.75, 35.37, 30.52, 30.50, 28.78, 26.97, 21.40, 21.24;and
   (b) $^1H$ NMR chemical shifts, as measured in $CD_3OD$: 7.24 (m, 4H), 7.12 (m, 6H), 6.22 (d, 2.0), 5.43 (dt, 15.0 6.5), 5.36 (dt, 15.0, 6.5), 5.31 (dd, 15.0, 7.5), 5.30 (dd, 15.0, 7.5), .5.24 (s), 4.03 (d, 2.0), 2.56 (m, 4H), 2.33 (m, 3H), 2.27 (m, 3H), 2.07 (sext, 7.0, 2E), 1.94 (m, 2H), 1.57 (m, 4H), 1.28 (m, 4H), 0.94 (d, 6.0, 3H), 0.93 (d, 6.5, 3H).

10. A compound of molecular formula $C_{38}H_{54}O_{14}$ and molecula weight 734 characterized by the
   (a) $^{13}C$ NMR chemical shifts as measured in $CD_3OD$: 173.18, 173.05, 172.5, 170.38, 168.73, 143.93, 138.83, 129.42 (2), 129.27 (2), 127.66, 126.64, 107-12, 91.0, 82.36, 81.30, 76.73, 75.69, 75.65, 37.84, 37.64, 36.93, 36.51, 35.40, 35.32, 35.19, 32.97, 30.57, 30.48, 30.34, 28.82, 26.48, 23.69, 21.25, 21.20, 19.75, 14.41; and
   (b) $^1H$ NMR chemical shifts as measured in $CD_3OD$: 7.23 (m, 2H), 7.12 (m, 3H), 6.22 (d, 2.0), 5.37 (dt, 15.1, 6.0), 5.31 (dd, 15.1, 7.5), 5.23 (s), 4.88 (m), 4.02 (d, 2.0), 2.56 (m, 2H), 2.34 (m, 2H), 2.26 (m, 2H), 2.07 (sext, 6.9), 2.02 (s, 3H), 1.88 (m, 2H), 1.58 (m, 8H), 1.3 (m, 12H), 0.93 (d, 7.0, 3H), 0.89 (t, 6.9, 3H).

11. A pharmaceutical composition comprising a nontoxic therapeutically effective amount of a compound of claim 1 and a pharmaceutically acceptable carrier.

12. A pharmaceutical composition comprising a nontoxic therapeutically effective amount of a compound of claim 1 in combination with a pharmaceutically acceptable nontoxic cationic polymer capable of binding bile acids in a non-reabsorbable form in the gastrointestinal tract and pharmaceutically acceptable carrier.

13. A pharmaceutical composition comprising a nontoxic apeutically effective amount of a compound of claim 1/in combination with a nontoxic therapeutically effective amount of a cholesterol lowering agent selected from the group consisting of:
   (a) HMG-COA reductase inhibitor;
   (b) HMGOCOA synthase inhibitor;
   (c) Squalene expoxidase inhibitor;
   (d) Probucol;
   (e) Niacin;
   (f) Gemfibrozil; and
   (g) Clofibrate.

14. A composition of claim 13 wherein the composition comprises a compound of claim 1 and an HMG-CoA reductase inhibitor.

15. A composition of claim 14 wherein the HMG-CoA reductase inhibitor is selected from lovastatin, simvastatin, pravastatin and fluvastatin.

16. A method of treating hypercholesterolemia comprising the administration to a subject in need of such treatment a nontoxic therapeutically effective amount of the compound of claim 1.

17. A method of inhibiting squalene synthetase comprising the administration to a subject in need of such treatment a nontoxic therapeutically effective amount of a compound of claim 1.

18. A method for inhibiting fungal growth comprising applying to the area where growth is to be controlled an anti-fungally effective amount of a compound of claim 1.

* * * * *

UNITED STATES PATENT AND TRADEMARK OFFICE
CERTIFICATE OF CORRECTION

PATENT NO. : 5,260,332
DATED : November 9, 1993
INVENTOR(S) : Claude Dufresne

It is certified that error appears in the above-identified patent and that said Letters Patent is hereby corrected as shown below:

On the cover page, please correct the name of the Assignee from " Merci & Co., Inc., Rahway, N.J." to -- Merck & Co., Inc., Rahway, N.J. --.

At Col. 13, Claim 8, line 43, please change "19.83" to --19.82 --.

At Col. 14, Claim 9, line 3, please change "(sext, 7.0, 2E)" to -- (sext, 7.0, 2H) --.

At Col. 14, Claim 13, line 31, after the word toxic, please change "apeutically" to -- therapeutically --.

Signed and Sealed this

Thirty-first Day of May, 1994

Attest:

BRUCE LEHMAN

Attesting Officer     Commissioner of Patents and Trademarks